US010653838B2

(12) United States Patent
Fabien et al.

(10) Patent No.: US 10,653,838 B2
(45) Date of Patent: May 19, 2020

(54) AUTO-INJECTOR WITH A DELAY DEVICE COMPRISING AN EPICYCLIC GEAR TRAIN

(71) Applicant: APTAR FRANCE SAS, Le Neubourg (FR)

(72) Inventors: David Fabien, Plouarzel (FR); Thomas Gomez, Saint Aubin de Medoc (FR); Anthony Saussaye, Louviers (FR); Olivier His, Saint Etienne du Vauvray (FR)

(73) Assignee: APTAR FRANCE SAS, Le Neubourg (FR)

( * ) Notice: Subject to any disclaimer, the term of this patent is extended or adjusted under 35 U.S.C. 154(b) by 40 days.

(21) Appl. No.: 15/575,870

(22) PCT Filed: Jun. 2, 2016

(86) PCT No.: PCT/FR2016/051318
§ 371 (c)(1),
(2) Date: Nov. 21, 2017

(87) PCT Pub. No.: WO2016/193627
PCT Pub. Date: Dec. 8, 2016

(65) Prior Publication Data
US 2018/0140775 A1 May 24, 2018

(30) Foreign Application Priority Data
Jun. 5, 2015 (FR) ...................... 15 55156

(51) Int. Cl.
*A61M 5/20* (2006.01)
*A61M 5/315* (2006.01)
*A61M 5/32* (2006.01)

(52) U.S. Cl.
CPC ............ *A61M 5/20* (2013.01); *A61M 5/2033* (2013.01); *A61M 5/3157* (2013.01);
(Continued)

(58) Field of Classification Search
CPC .. A61M 2005/2013; A61M 2005/2073; A61M 2005/2086; A61M 2205/58;
(Continued)

(56) References Cited

U.S. PATENT DOCUMENTS

2013/0317435 A1* 11/2013 Fabien ................ A61M 5/2033
604/135

FOREIGN PATENT DOCUMENTS

WO   2013/078200 A1   5/2013
WO   2013/175139 A1   11/2013
(Continued)

OTHER PUBLICATIONS

English Translation of the International Preliminary Report on Patentability dated Dec. 21, 2017, in counterpart International Application No. PCT/FR2016/051318.
(Continued)

*Primary Examiner* — Brandy S Lee
(74) *Attorney, Agent, or Firm* — Sughrue Mion, PLLC (57) ABSTRACT

An autoinjector having a body (1) receiving a reservoir (S), the reservoir containing fluid and including a piston (P), such as a pre-filled syringe, and stationary in said body (1); a piston rod (5) that co-operates with the piston (P), the piston rod (5) movable between a primed position and an injection position in which the piston rod has moved the piston so as to inject the fluid into an injection site; and a visual, audible, and/or tactile indicator device for indicating to the user that the autoinjector may be removed from the injection site, the indicator device arranged at the rear end of the body (1), remote from the injection site. The autoinjector includes a retarding device to delay actuating the indicator device relative to the end of injection, the retarding device having an epicyclic gear train having at least one stage, and advantageously two stages.

12 Claims, 13 Drawing Sheets

(52) U.S. Cl.
CPC ..... *A61M 5/326* (2013.01); *A61M 2005/2013* (2013.01); *A61M 2005/2073* (2013.01); *A61M 2005/2086* (2013.01); *A61M 2205/58* (2013.01); *A61M 2205/581* (2013.01); *A61M 2205/582* (2013.01); *A61M 2205/583* (2013.01)

(58) Field of Classification Search
CPC ...... A61M 2205/581; A61M 2205/582; A61M 2205/583; A61M 5/20; A61M 5/2033; A61M 5/3157; A61M 5/326
See application file for complete search history.

(56) References Cited

FOREIGN PATENT DOCUMENTS

| | | |
|---|---|---|
| WO | 2013/175140 A1 | 11/2013 |
| WO | 2013/175144 A1 | 11/2013 |

OTHER PUBLICATIONS

International Search Report of PCT/FR2016/051318 dated Sep. 19, 2016 [PCT/ISA/210].

* cited by examiner

AUTO-INJECTOR WITH A DELAY DEVICE COMPRISING AN EPICYCLIC GEAR TRAIN

CROSS REFERENCE TO RELATED APPLICATIONS

This application is a National Stage of International Application No. PCT/FR2016/051318, filed Jun. 2, 2016, claiming priority based on French Patent Application No. 15 55156, filed Jun. 5, 2015, the contents of all of which are incorporated herein by reference in their entirety.

The present invention relates to an autoinjector.

Autoinjectors are well known in the prior art. The purpose of such devices is mainly to inject the contents of a syringe automatically into a patient's body. Various systems exist for making the penetration of the needle into the body of the patient and the injection of the fluid contained in the syringe automatic. Autoinjectors are relatively complex devices that must satisfy a certain number of constraint requirements in order to be reliable. The robustness of the device, its handling, and its ease of use for the user are also important elements. In addition, since most autoinjectors are for single use, the cost of manufacture and of assembly is also a factor that needs to be taken into account.

Numerous autoinjectors exist on the market, but they present a certain number of drawbacks.

Thus, in particular when the volume of fluid is relatively large and/or when the injected fluid is relatively viscous, it is desirable to enable the fluid to diffuse from the injection site for a few seconds after said injection. When the user removes the autoinjector immediately after the end of injection, a fraction of the fluid may escape from the user's body, and this reduces the effectiveness of the treatment. It is thus desirable to make provision for the user to continue to hold the autoinjector against the body for a few seconds after the end of injection. This aspect is generally resolved in existing autoinjectors by the operating instructions that ask the user to count silently a certain number of seconds prior to removing the device. This is unreliable and thus unsatisfactory, since the system depends on the user who, in some circumstances, may be disturbed or weakened by the injection action that has just been performed.

Documents WO 2013/175139, WO 2013/175140, WO 2013/175144, and WO 2013/078200 describe prior-art autoinjectors.

An object of the present invention is to provide an autoinjector that does not have the above-mentioned drawbacks, and that makes it possible to satisfy the various major requirements and constraints for safe and reliable use of the autoinjector.

Another object of the present invention is to provide an autoinjector that is reliable in use, that enables the user to determine when the autoinjector must be removed or may be removed from the body after use, that is safe and that prevents any risk of injury, and that is simple and inexpensive to manufacture and to assemble.

The present invention thus provides an autoinjector comprising:
  a body receiving a reservoir, said reservoir containing fluid and including a piston, such as a pre-filled syringe, said reservoir being stationary in said body;
  a piston rod that is adapted to co-operate with the piston of said reservoir, said piston rod being movable between a primed position and an injection position in which said piston rod has moved the piston of the reservoir so as to inject the fluid into an injection site; and
  a visual, audible, and/or tactile indicator device for indicating to the user that said autoinjector may be removed from said injection site, said visual, audible, and/or tactile indicator device being arranged at the rear end of said body, remote from said injection site;
  said autoinjector including a retarding device so as to delay actuating said visual, audible, and/or tactile indicator device relative to the end of injection, said retarding device comprising an epicyclic gear train having at least one stage, and advantageously two stages.

Advantageously, said epicyclic gear train comprises a retarding spring, at least one planet carrier, each carrying at least one planet gear, a trigger, and a locking key so as to prevent said trigger from turning until the end of injection.

Advantageously, said retarding spring is made in the form of a spiral spring that is fastened firstly to a planet carrier or to the trigger and secondly to the body.

Advantageously, each planet gear of a planet carrier co-operates firstly with said body and secondly either with another planet carrier or with said trigger.

Advantageously, said body includes a ring gear on its inside surface, said ring gear co-operating with at least one planet gear.

Advantageously, said trigger includes a central pin that is provided with a sun gear that co-operates with at least one planet gear.

Advantageously, said epicyclic gear train comprises two planet carriers, each carrying three planet gears.

Advantageously, said locking key comprises a head, a longitudinal rod, and an endpiece that is adapted to co-operate with the piston rod.

Advantageously, prior to triggering the retarding system, the head of the locking key is in its blocking position in which it co-operates with a corresponding profile of the body and with a corresponding profile of the trigger, such that said trigger is prevented from turning relative to said body by said locking key.

Advantageously, when the piston rod arrives towards its end-of-injection position, it co-operates with the endpiece of the locking key so as to pull said locking key axially downwards out from its blocking position, such that said trigger is thus no longer prevented from turning by said locking key.

Advantageously, said trigger includes at least one flexible tab that is adapted to co-operate with said body so as to generate a noise and/or so as to brake the turning of said trigger.

Advantageously, said autoinjector includes an actuator sleeve that includes a contact end for coming into contact with the user's body, said actuator sleeve extending inside said body at least in part, and being movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector.

Advantageously, said reservoir includes a needle through which said fluid is injected into said injection site.

These characteristics and advantages and others of the present invention appear more clearly from the following detailed description, given by way of non-limiting examples, and with reference to the accompanying drawings, and in which.

In the following description, the terms "top", "bottom", "high", and "low" refer to the positions shown in FIGS. 1a to 6 and 15. The terms "axial" and "radial" refer to the longitudinal central axis X, shown in particular in FIG. 1a, that corresponds to the longitudinal axis of the needle.

The autoinjector is described below with reference to an advantageous embodiment. It should nevertheless be observed that autoinjectors, which are complex appliances, comprise a plurality of modules for performing a plurality of functions. The various modules may be used separately and independently of one another, without necessarily being combined with the other modules, and in particular they could be used in autoinjectors of shape that is different from the shape shown in the drawings. Furthermore, it should be observed that the drawings are diagrammatic views, which do not necessarily represent the exact shape of the components of an autoinjector, and they are not necessarily to scale, in particular for purposes of clarity. In addition, the drawings do not necessarily represent all of the component elements of an autoinjector, but only the elements necessary for operation of the present invention. Thus, various additional and/or complementary elements and modules could be associated with the autoinjector shown in the figures.

The autoinjector shown in the figures comprises a body 1 in which an actuator sleeve 10 slides axially, the actuator sleeve 10 having a bottom end 101 that is for coming into contact with the body of the patient around the injection zone. In the embodiment shown in the figures, the autoinjector includes a lower body 1a, an intermediate body 1b, and an upper body 1c that are assembled together so as to form the body 1 of the autoinjector, as indicated in FIG. 1b. Below, and in the other figures, the term "body" and the numerical reference "1" are used to designate said unitary body formed by assembling said lower body 1a with said intermediate body 1b and said upper body 1c. It should be observed that the body 1 could be formed of any number of body portions, e.g. two, and that the embodiment in the figures, with three body portions, is not limiting.

A reservoir S may be inserted into said body 1 of the autoinjector, said reservoir S being stationary in said body 1. The reservoir S contains fluid and includes a piston P and a needle A. The piston P is adapted to move in said reservoir S so as to inject the fluid through said needle A. Optionally, the present invention could also apply to a reservoir that does not have a needle, in particular in an injection device that does not have a needle.

The present description is made with reference to a syringe S that may be of any type. More generally, it is understood that the term "syringe" in the present description encompasses any type of reservoir associated with a needle. Preferably, the reservoir S is a pre-filled syringe.

Before the autoinjector is actuated, the needle A of the syringe S can be protected by a guard (not shown), the autoinjector possibly including a cap (not shown) that the user can remove before actuation. Removal of the cap advantageously causes the guard to be removed.

Figure 1A:
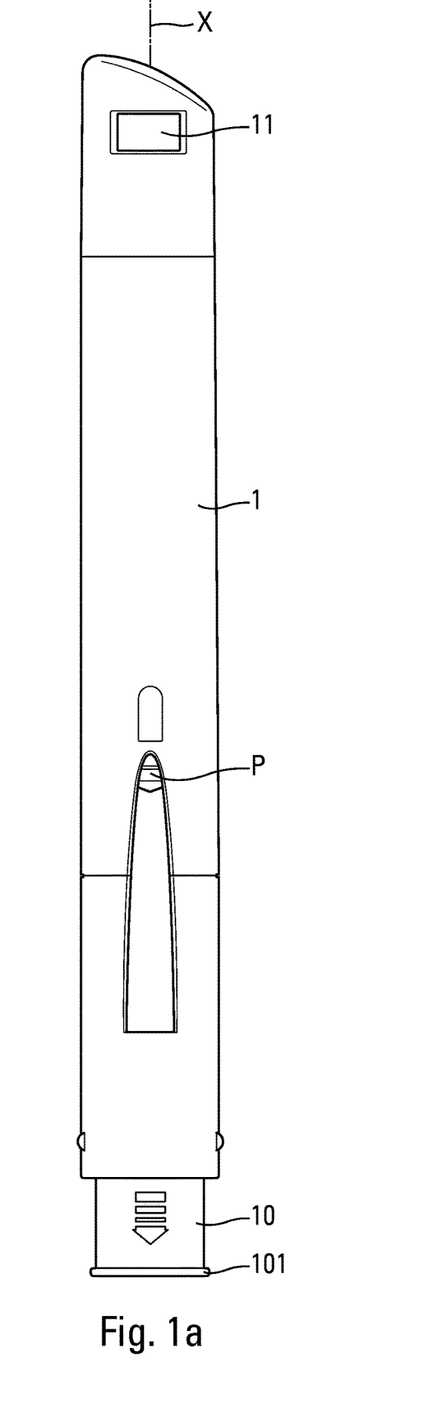
FIGS. 1a and 1b are diagrammatic views, respectively from the side and in section, of an autoinjector constituting an advantageous embodiment of the present invention, in its rest position, before-pricking.
Figure 1B:
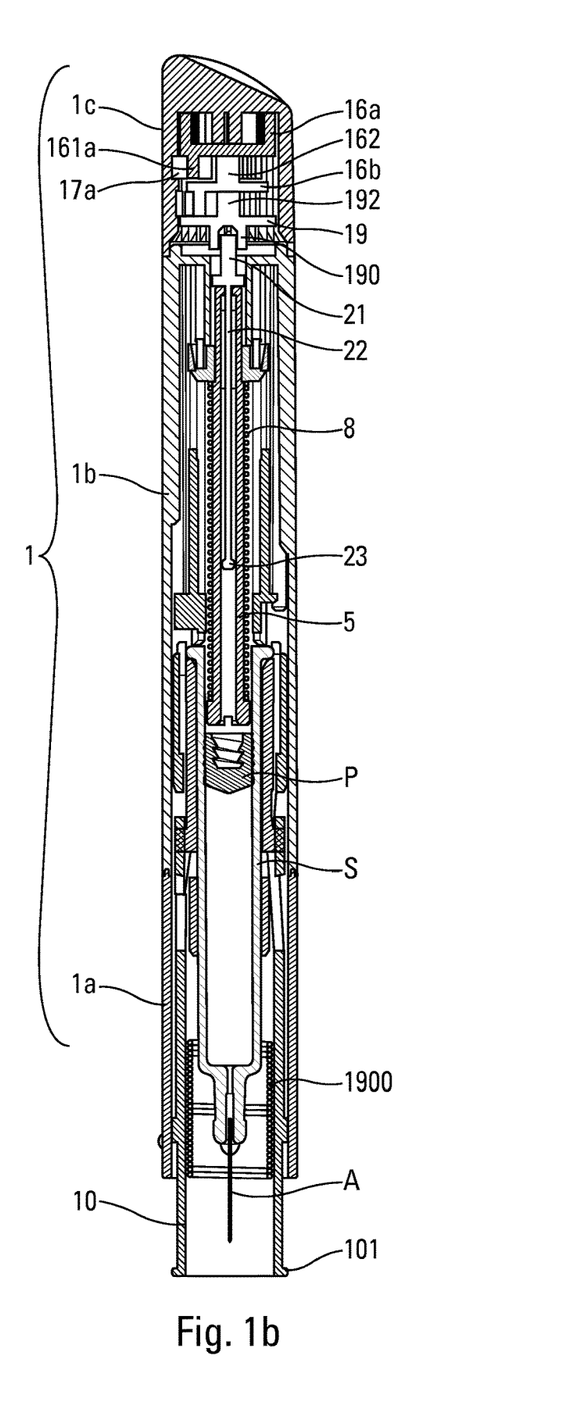
Figure 2A:
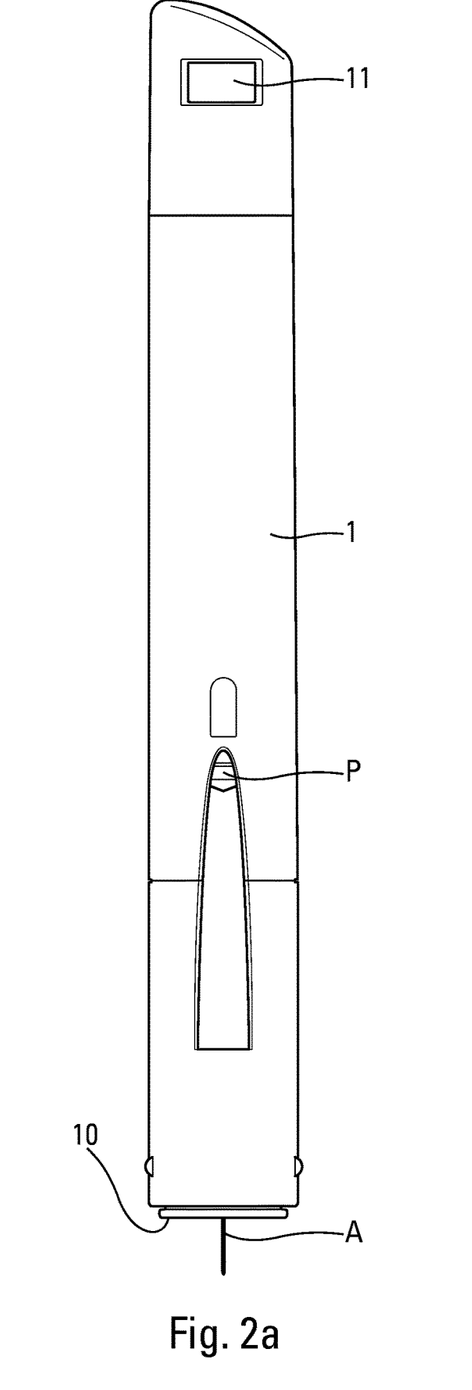
FIGS. 2a and 2b are views similar to the views in FIGS. 1a and 1b, in the after-pricking and before-injection position.
Figure 2B:
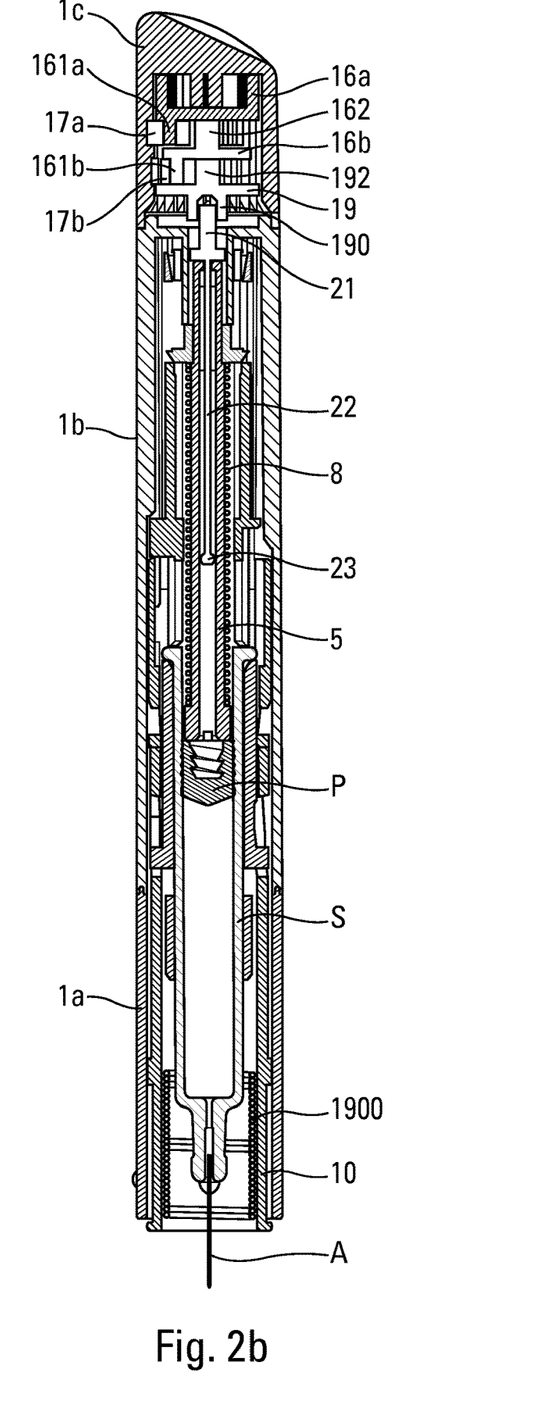
Figure 3A:
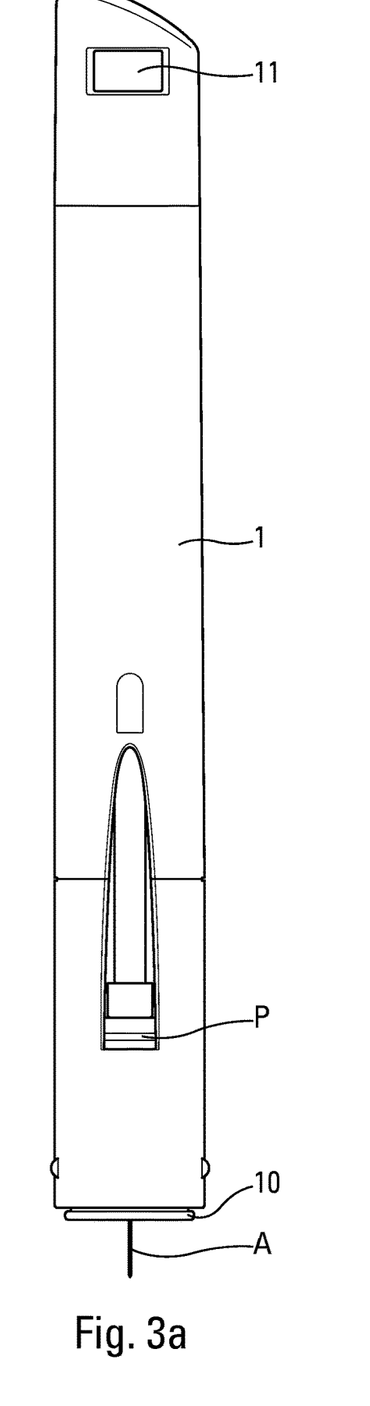
FIGS. 3a and 3b are views similar to the views in FIGS. 2a and 2b, in the just prior to the end of injection position and at the moment at which the retarding system is triggered.
Figure 3B:
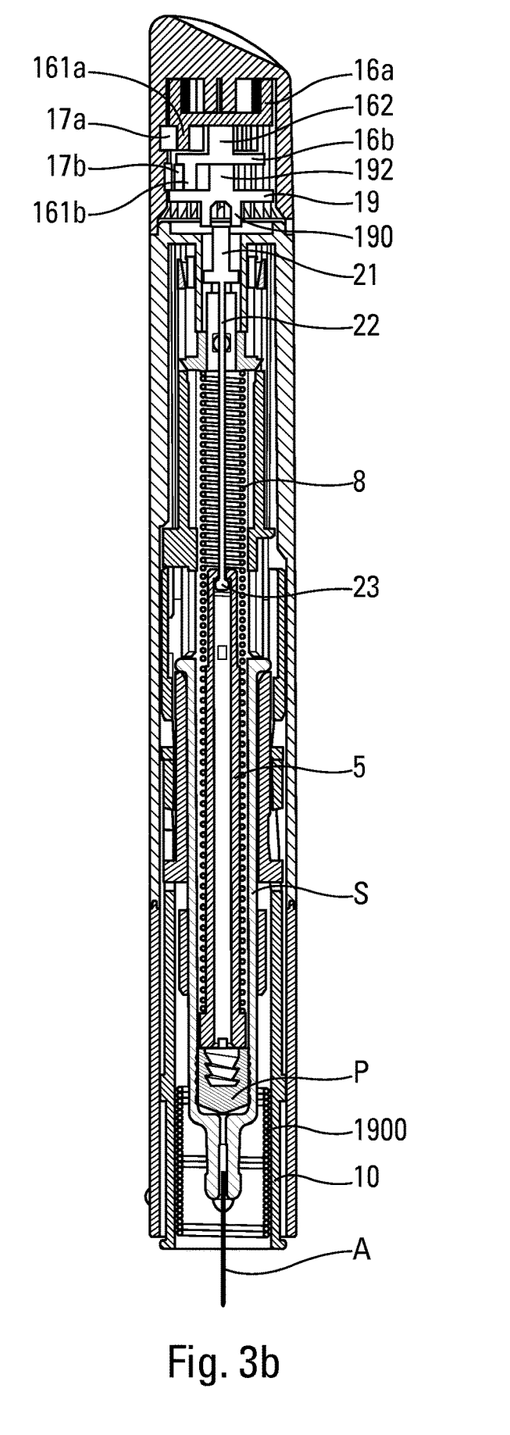
Figure 4A:
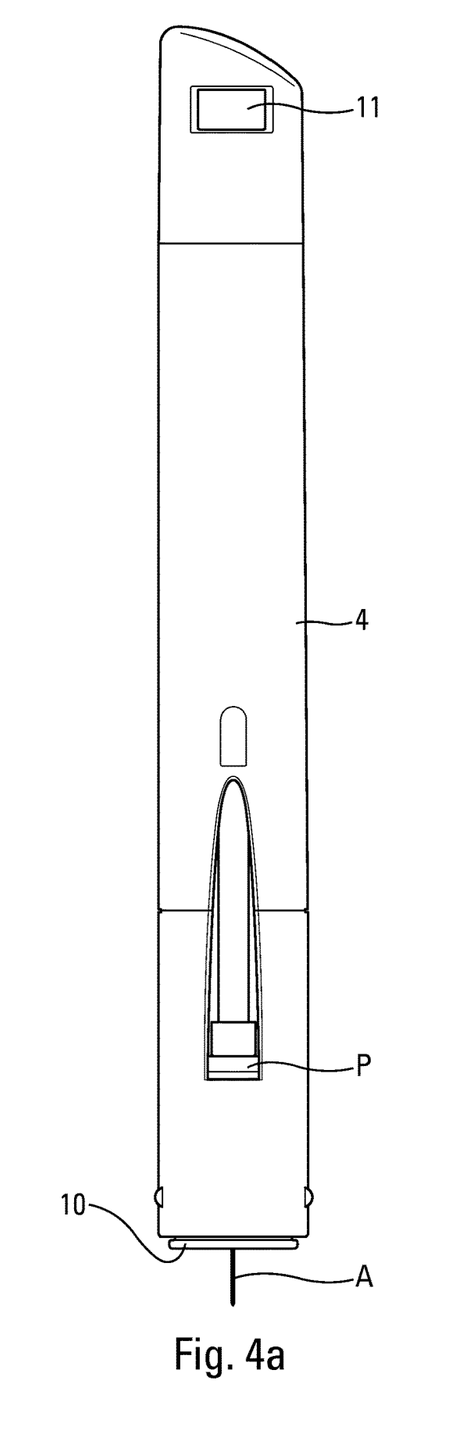
FIGS. 4a and 4b are views similar to the views in FIGS. 3a and 3b, in the end-of-injection position and after the retarding system has been triggered.
Figure 4B:
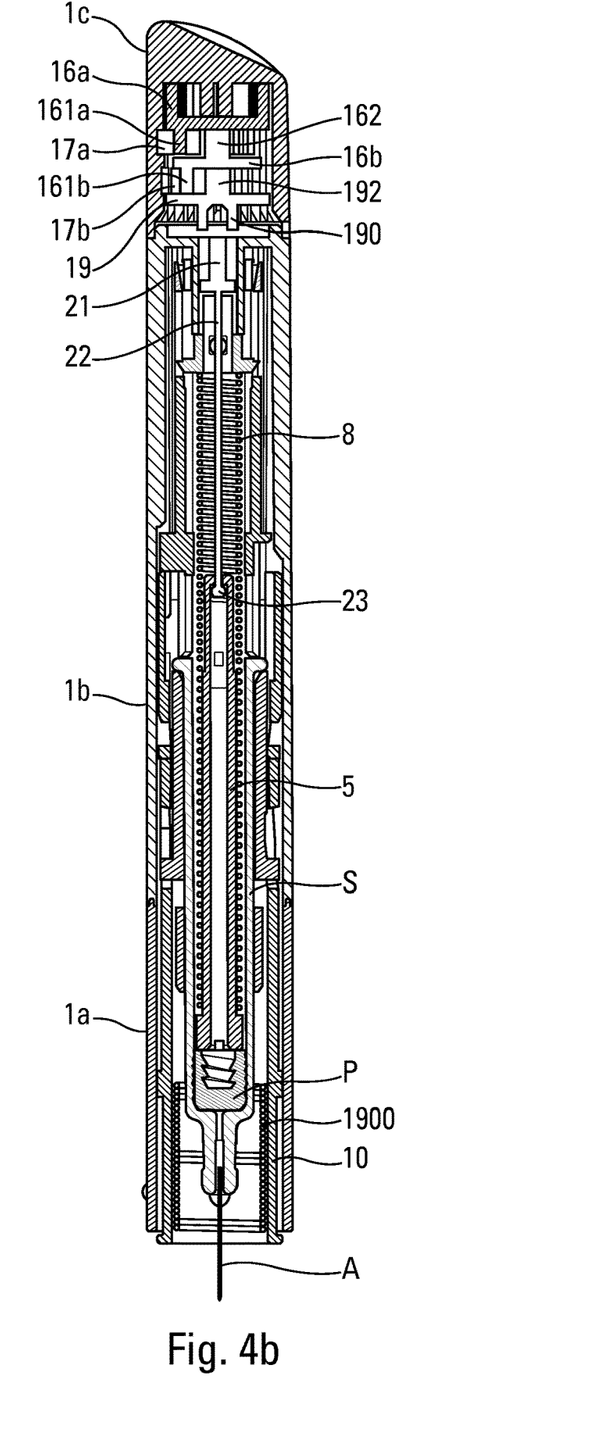
Figure 5A:
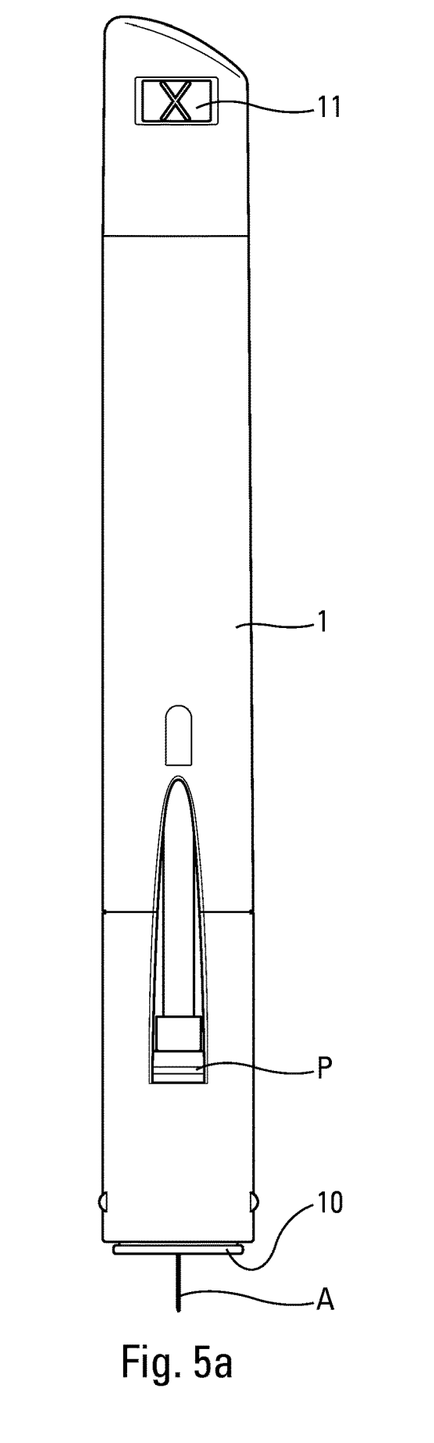
FIGS. 5a and 5b are views similar to the views in FIGS. 4a and 4b, in the end of actuating position of the retarding system, before the autoinjector has been removed from the injection site.
Figure 5B:
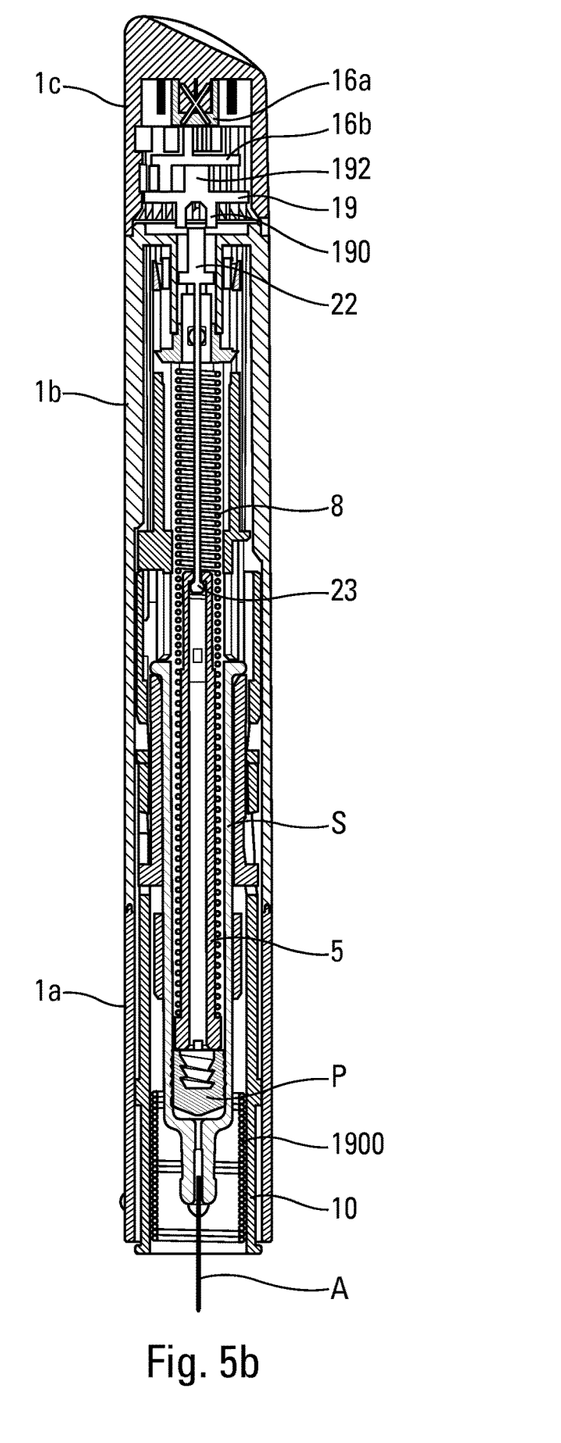

Before actuation, the actuator sleeve 10 is in a first projecting position in which it surrounds the needle A, as shown in FIGS. 1a and 1b. During actuation, the actuator sleeve 10 slides inside the body 1 towards an actuated position, so as to expose the needle A and enable pricking, and then injection of the fluid.

Figure 6:
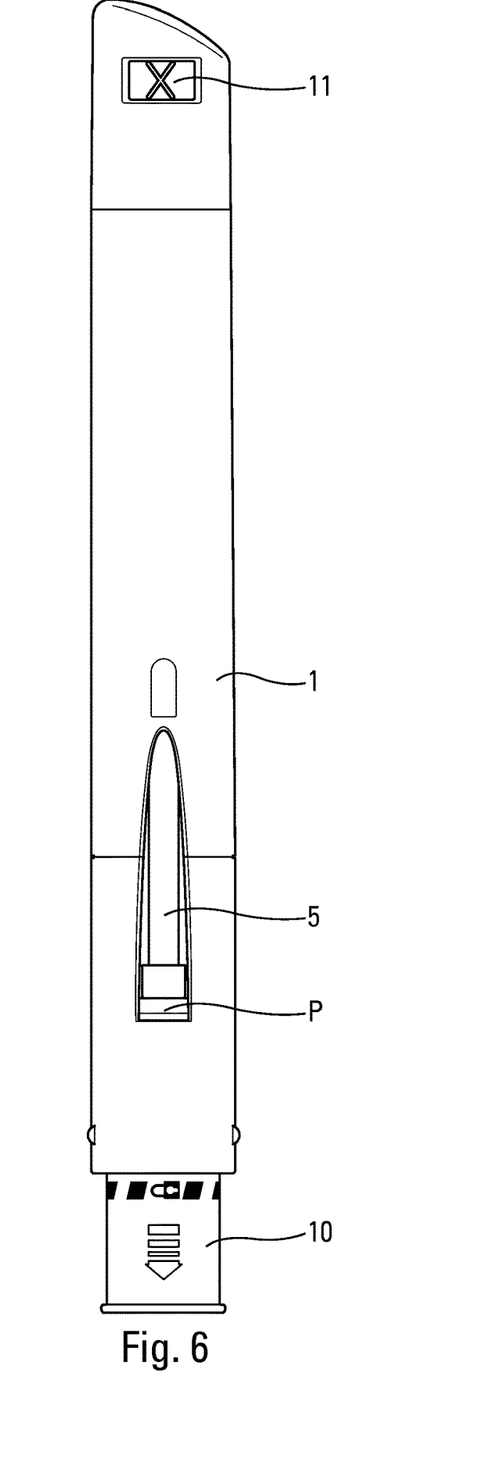
FIG. 6 is a view similar to the view in FIG. 5a, in the end-of-use position, after the autoinjector has been removed from the injection site.

After injection, when the user removes the autoinjector from the injection site, the actuator sleeve 10 returns into an end-of-use second projecting position in which it is once again arranged around the needle A, so as to avoid any risk of injury with said needle, as shown in FIG. 6.

The actuator sleeve 10 is advantageously urged towards its projecting positions by a resilient member or spring 1900 that may be of any type. Advantageously, in said end-of-use position, said actuator sleeve 10 is locked, and can no longer be moved axially into said body 1. By way of example, locking may be achieved by tabs (not shown) that are secured to the body 1 or to the reservoir S, and that co-operate with openings (not shown) in said actuator sleeve 10 when said actuator sleeve reaches its second projecting position. Locking, that is not essential to the operation of the present invention, is not described in greater detail below. It could be achieved in ways that are different from the particular embodiment mentioned above. In particular, it could be achieved in accordance with the teaching of documents WO 2013/175140 or WO 2013/175142. The autoinjector also includes an automatic injection system, in particular comprising a piston rod 5 that is adapted to co-operate with the piston P so as to move it in the reservoir S so as to dispense the fluid through the needle A. Conventionally, the piston rod 5 is urged by an injection spring 8 towards its dispensing position and, before actuation, it is held in its rest position by an appropriate injection lock.

An advantageous injection lock is described in particular in document WO 2015/155484.

The lock may include at least one blocking element that is held in its blocking position by a blocking ring. Triggering said injection lock causes said injection means to be actuated, and thus fluid to be injected through the needle. Said injection lock may further include a control sleeve 4 that is arranged in said body 1, said control sleeve 4 containing said piston rod 5 and said injection spring 8, said piston rod 5 including a radial recess that receives at least one blocking element that is movable between a blocking position and an unblocking position. Said at least one blocking element is preferably of shape that is substantially spherical, such as a ball. Advantageously, said balls are urged radially outwards by said piston rod 5 and they are held in their blocking position by the blocking ring. The blocking ring is axially movable relative to said piston rod 5 between a locking position in which it holds said balls in their blocking position, and an unlocking position in which said balls are released, thus unblocking said injection lock and enabling said injection spring 8 to move said piston rod 5 towards its injection position.

When the needle A of the syringe S has penetrated the user's body, the blocking ring is moved axially upwards, thereby causing the balls to be released from their blocking position, said balls then moving radially outwards. The piston rod 5 is then no longer held by the balls, and it is thus moved axially downwards so as to inject the fluid.

The autoinjector includes a visual, audible, and/or tactile indicator device for indicating to the user, in particular by an audible sound, by vibration, and/or by visual and/or tactile indication, that the autoinjector may be removed from the injection site. Said visual, audible, and/or tactile indicator device is arranged at the rear end of said body 1, remote from said injection site. In particular, in the embodiment shown, the indicator device includes an indicator element that gives both visual indication, by a suitable display 160 in one or more windows 11 of the body 1, and audible indication, as described in greater detail below.

In order to avoid the user removing the autoinjector from the injection site as soon as injection ends, the autoinjector includes a retarding system that delays actuating said indicator device relative to the end of injection.

Figure 17:
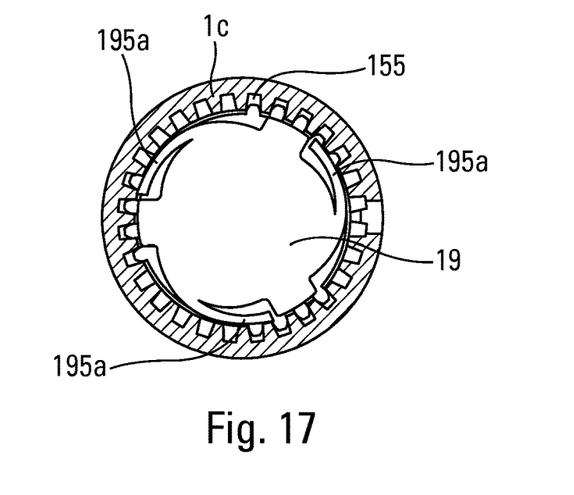
FIG. 17 is a diagrammatic section view on section plane E-E in FIG. 15, showing an advantageous variant embodiment.
Figure 19:
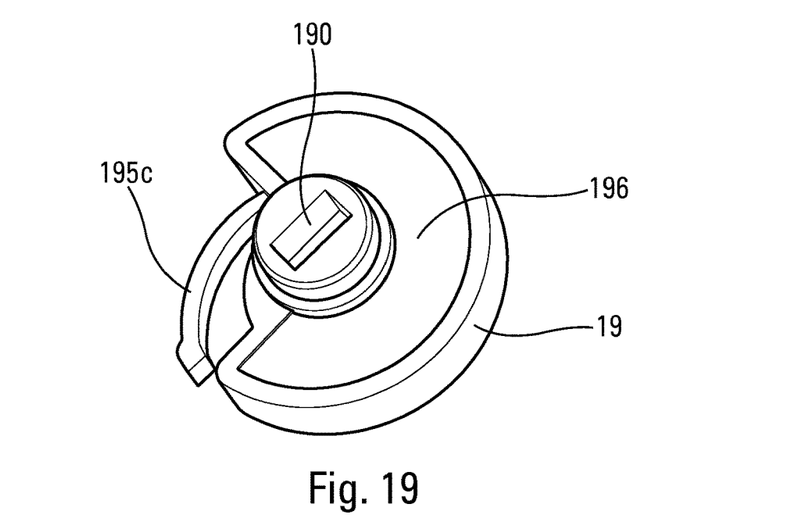
FIG. 19 is a perspective view of a detail of still another variant embodiment.

FIGS. 7 to 19 show an advantageous retarding system. FIGS. 7 to 16d show an advantageous embodiment of the present invention, and FIGS. 17 to 19 show advantageous variants.

The main purpose of the retarding system is to put off starting the visual, audible, and/or tactile indication after the end of injecting the fluid into said body. In particular, this enables the fluid to diffuse for a few seconds after it has been injected. Such a retarding system also provides a benefit for the user, who no longer has to count, e.g. up to 10, after being injected, where it is possible that the time taken to perform such counting might vary greatly from one user to another. With a retarding system, the sequence of using an autoinjector is facilitated.

The mechanical retarding system shown in FIGS. 7 to 19 thus makes it possible to put off starting the end-of-use indicator by a few seconds relative to the end of injection, this delay being predeterminable.

Figure 7:
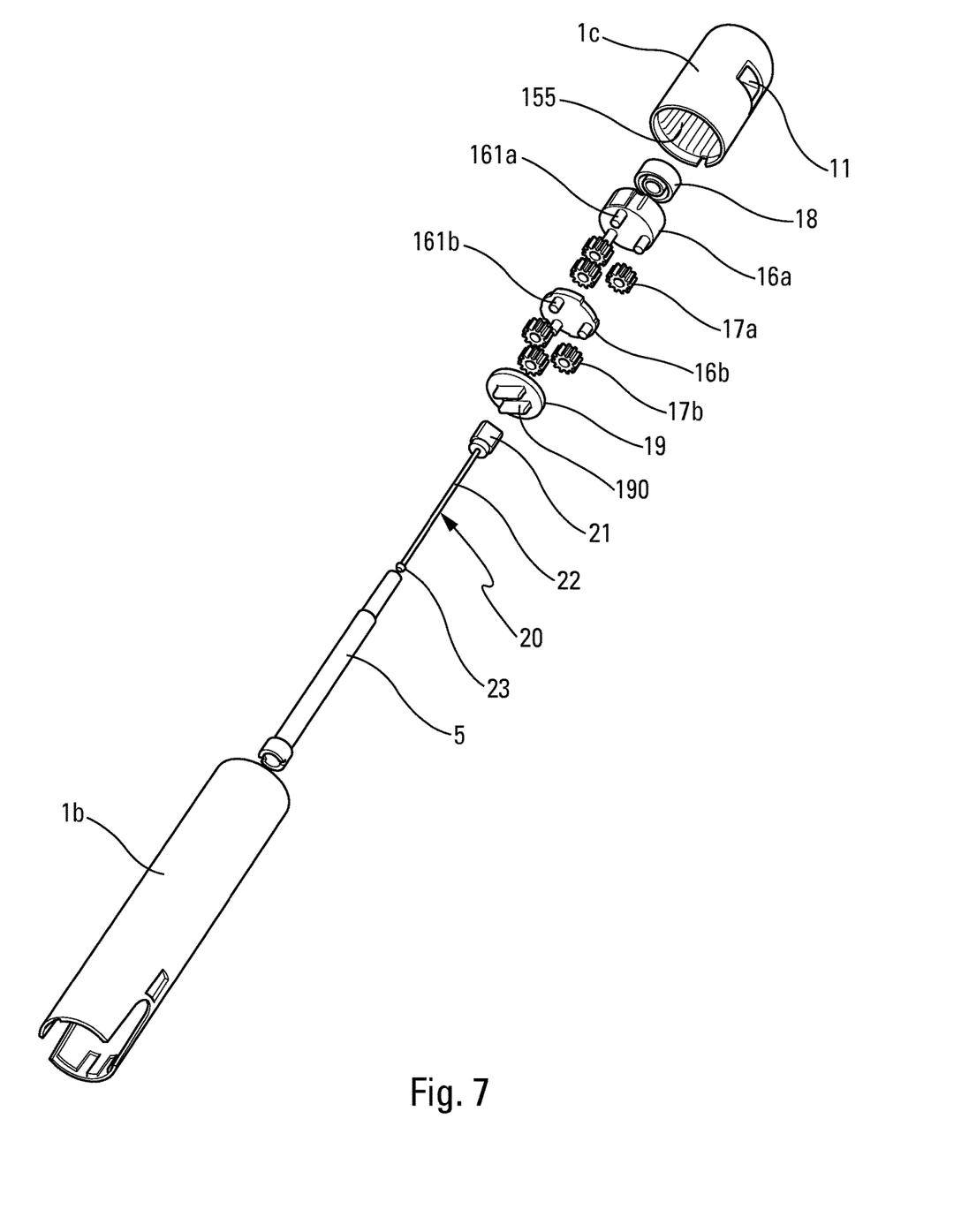
FIG. 7 is an exploded perspective view of the retarding system.
Figure 8:
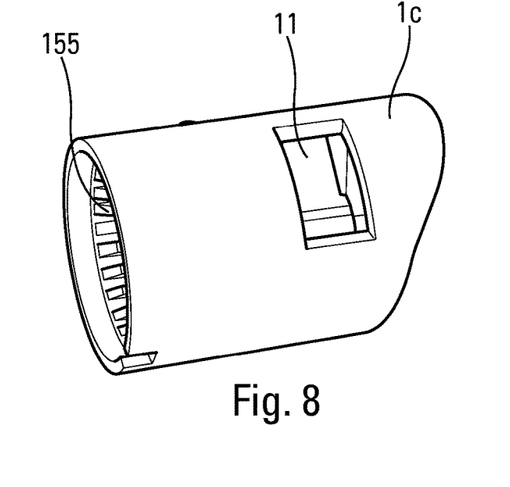
FIG. 8 is a perspective view of a detail of the upper body.
Figure 9:
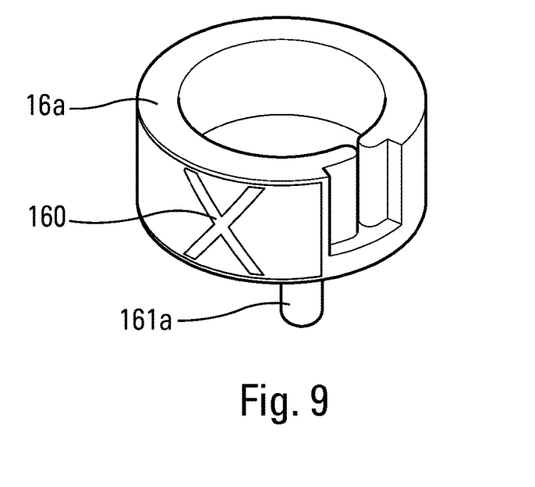
FIG. 9 is a perspective view of a detail of the indicator element of the visual, audible, and/or tactile indicator device.
Figure 10:
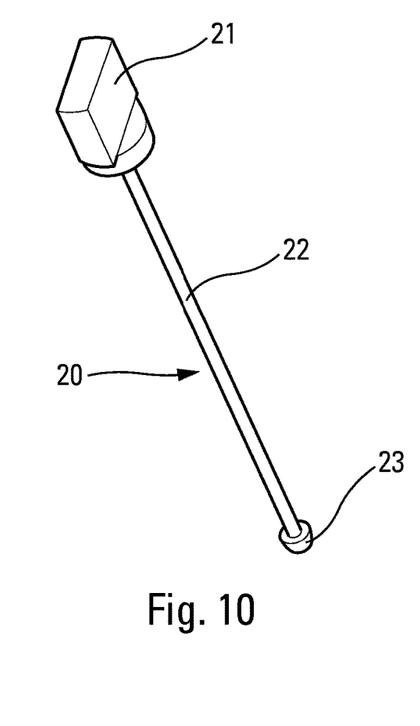
FIG. 10 is a perspective view of a detail of the locking key.
Figure 11:
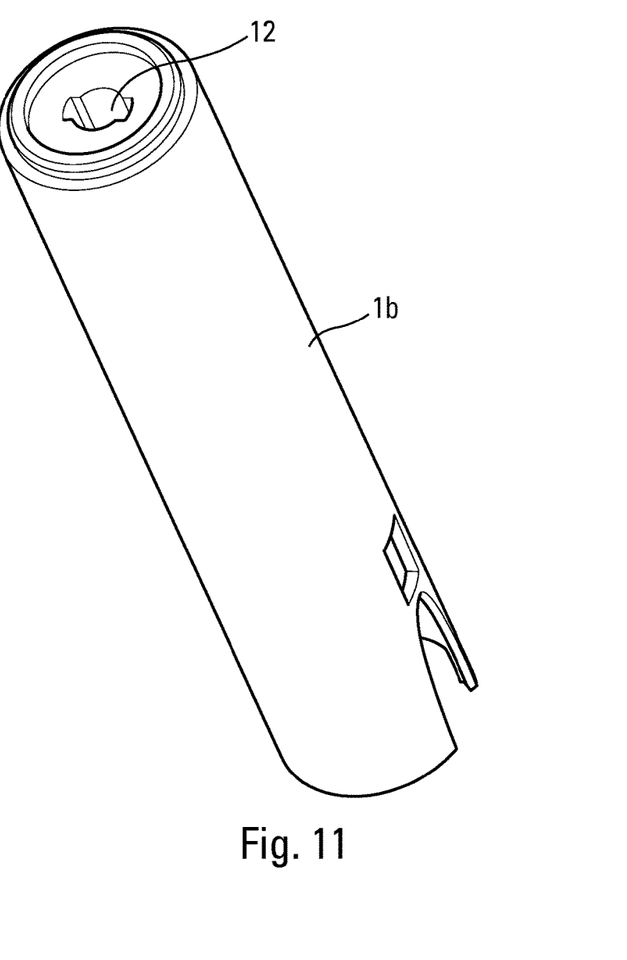
FIG. 11 is a perspective view of a detail of the intermediate body.
Figure 12A:
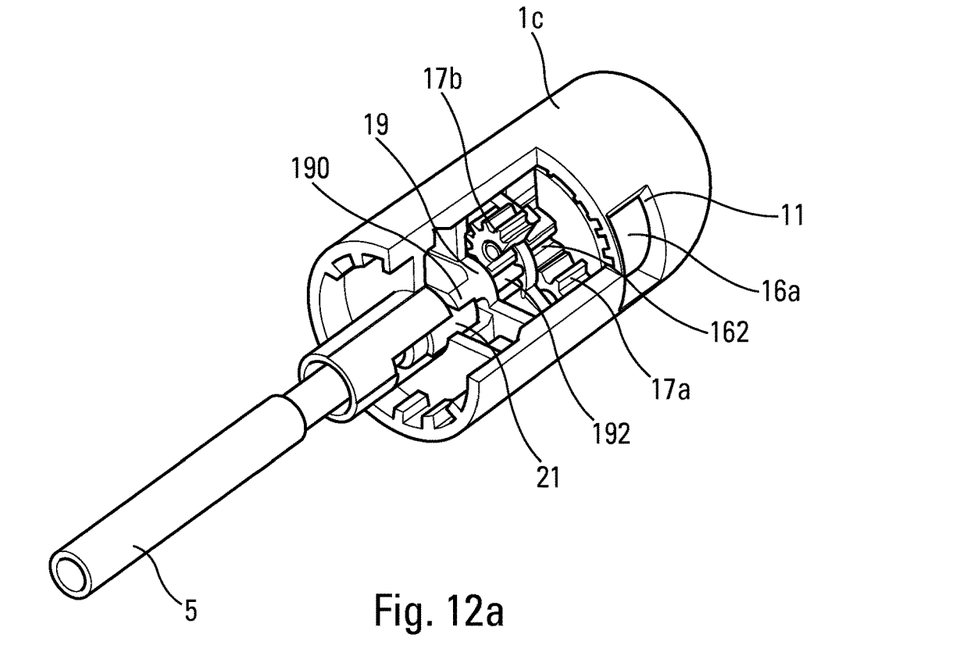
FIGS. 12a and 12b are diagrammatic views, respectively an exploded perspective view and a perspective view in section, of the retarding system of an advantageous embodiment of the present invention, in the position in FIGS. 1a and 1b.
Figure 12B:
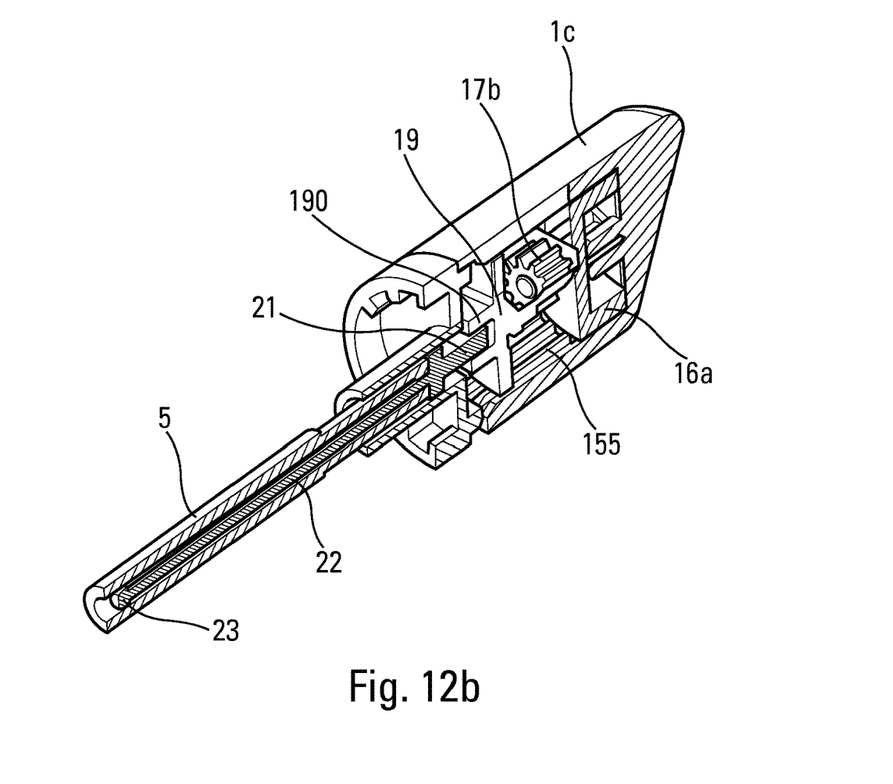
Figure 13A:
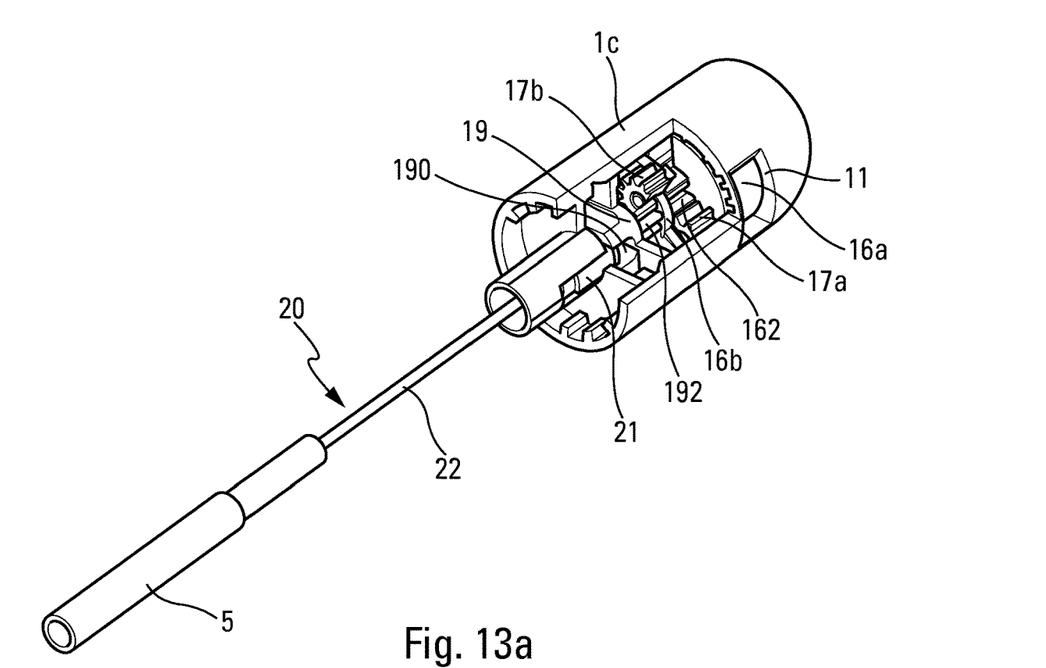
FIGS. 13a and 13b are views similar to the views in FIGS. 12a and 12b, in the position in FIGS. 3a and 3b.
Figure 13B:
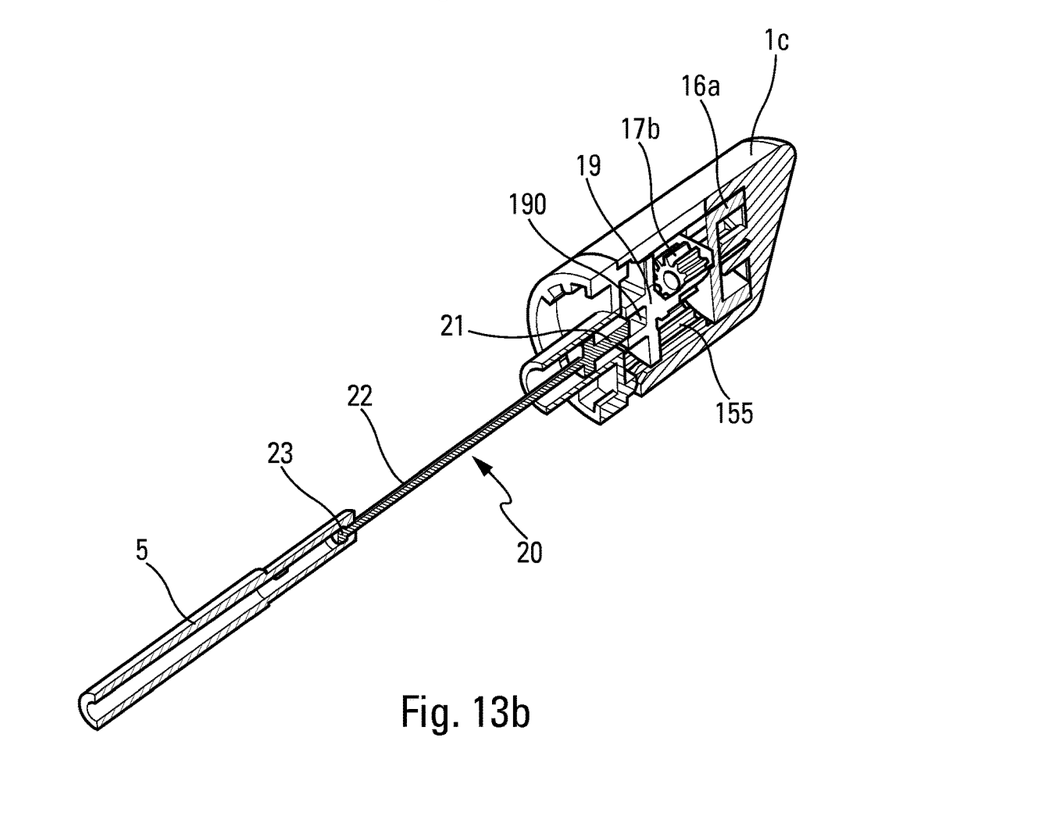
Figure 14:
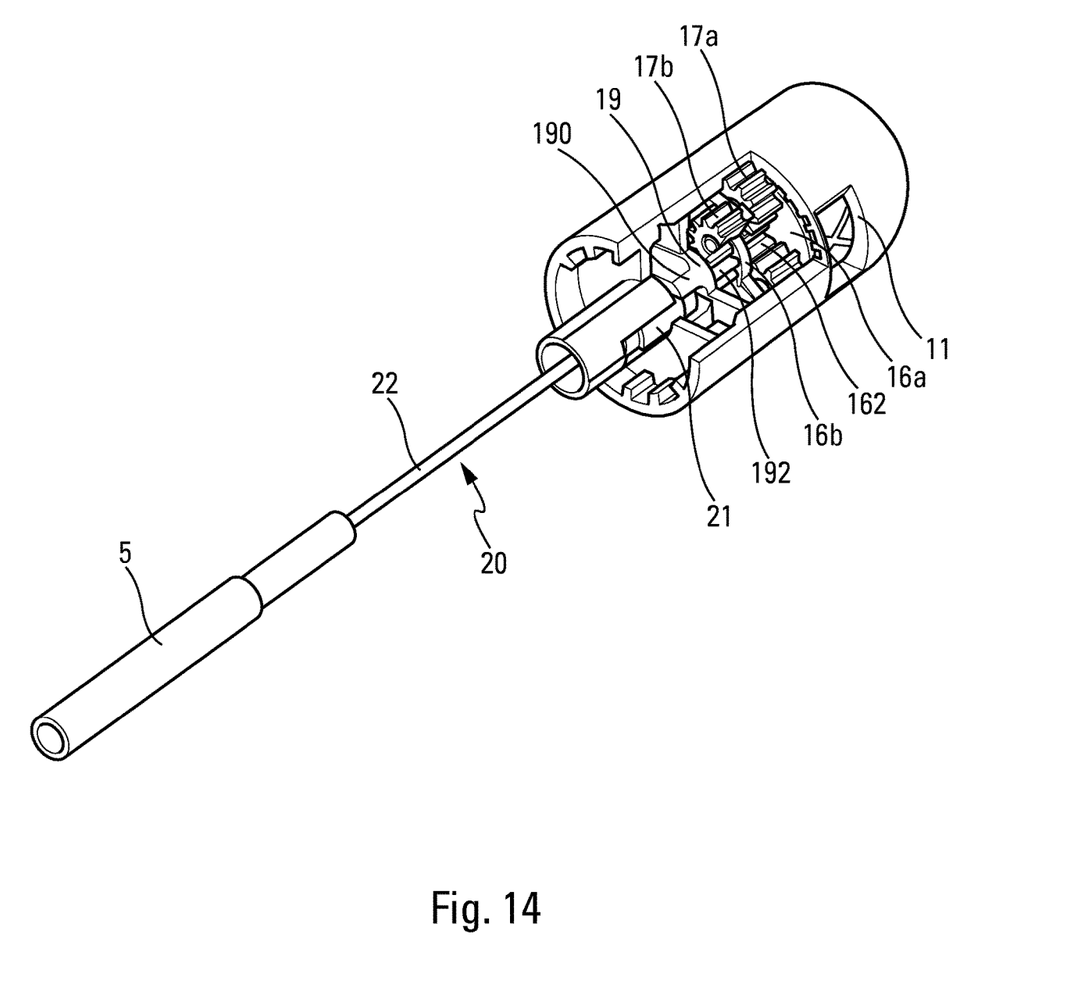
FIG. 14 is a view similar to the view in FIG. 13a, in the position in FIGS. 5a and 5b.
Figure 15:
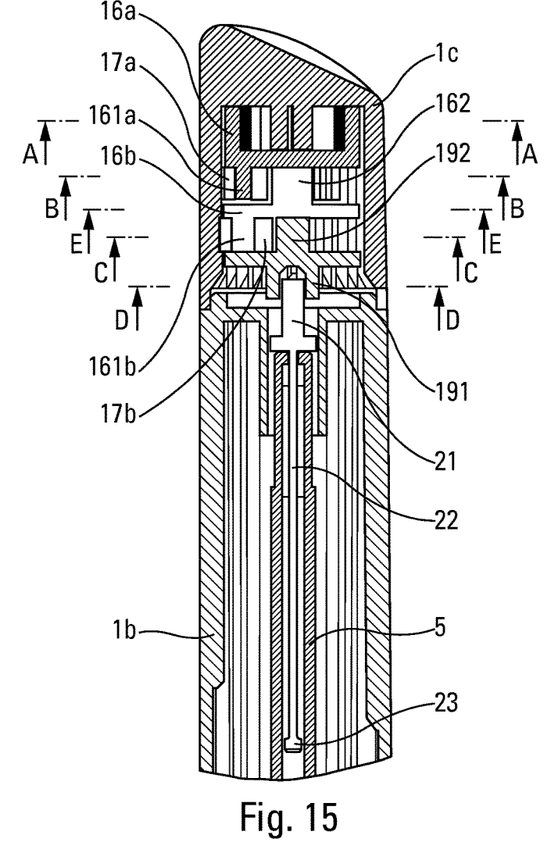
FIG. 15 is a diagrammatic section view of a detail of a portion of the autoinjector in FIGS. 1 to 6, more particularly showing the retarding system, in the position in FIGS. 1b and 2b.

FIG. 7 is an exploded perspective view of the retarding system of an advantageous embodiment. The retarding system comprises the upper body 1c, a retarding spring 18, preferably made in the form of a spiral spring, at least one planet carrier 16a, 16b, each carrying at least one planet gear 17, a trigger 19, a locking key 20, the piston rod 5, and the intermediate body 1b.

Each planet carrier 16a, 16b associated with its planet gears 17 forms a stage of the retarding system. In the embodiment shown in FIGS. 7 to 19, there are two stages stacked axially, with a first planet carrier 16a and a second planet carrier 16b, but any number of stages could be provided, e.g. a single stage or more than two stages.

Figure 16A:
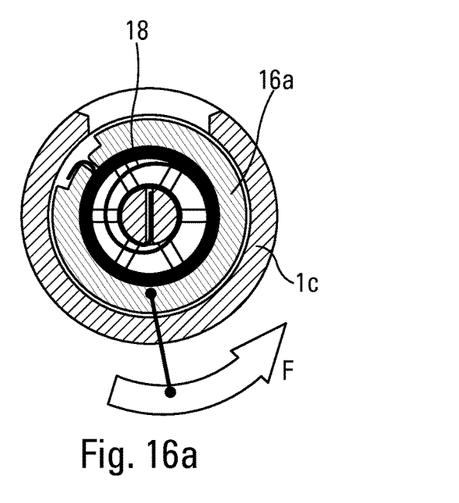
FIGS. 16a to 16d are diagrammatic section views, respectively on section planes A-A, B-B, C-C, and D-D in FIG. 15.

The spiral spring 18 is fastened firstly to the first planet carrier 16a and secondly to the upper body 1c, as can be seen in FIG. 16a. In a variant, said spiral spring could be fastened to another planet carrier, e.g. the second planet carrier 16b in the embodiment shown, or to the trigger 19. Furthermore, the spiral spring could be fastened to another portion of the body 1, e.g. the intermediate body 1b, or to any element that is fastened to said body 1.

In the embodiment shown, the first planet carrier 16a also forms the indicator element of the visual, audible, and/or tactile indication. In a variant, the indicator element could be formed by another planet carrier, e.g. the second planet carrier 16b in the embodiment shown, or by the trigger.

Each planet carrier 16a, 16b comprises a disk-shaped portion on which there are formed, on one side, one or more planet gear support pins 161a, 161b each receiving a planet gear 17a, 17b in rotary manner. In the embodiment shown, there are three planet gears 17a, 17b at each stage, such that there are three pins 161a, 161b on each planet carrier 16a, 16b. However, any number of planet gears is possible.

On the axial side remote from the support pins 161b, the second planet carrier 16b includes a central pin 162 that is provided with a sun gear, and that co-operates with the planet gears 17a of the first planet carrier 16a.

Thus, as can be seen in FIGS. 7 and 12a to 16d, the retarding system uses the principle of epicyclic gear trains. Each stage of the system makes it possible to decrease and/or slow down the turning of the preceding stage.

The locking key 20 comprises a head 21 that is adapted to co-operate with the retarding system, a longitudinal rod 22, and an endpiece 23 that is adapted to co-operate with the piston rod 5.

In the position prior to triggering the retarding system, the head 21 of the locking key 20 is in its blocking position in which it co-operates with a corresponding profile 12 of the intermediate body 1b and with a corresponding profile 190 of the trigger 19, such that said trigger is prevented from turning by said key. When the piston rod 5 comes towards its end-of-injection position, it co-operates with the endpiece 23 of the locking key 20, and thus pulls said locking key axially downwards. As a result, the head 21 of said locking key 20 moves axially out from said profile 190 of the trigger 19, such that said trigger 19 is no longer prevented from turning by said key 20.

On the axial side remote from said profile 190, the trigger includes a central pin 192 that is provided with a sun gear, and that co-operates with the planet gears 17b of the second planet carrier 16b.

If there was only a single stage instead of the two shown, the second planet carrier 16b would not exist, and the planet gears 17a of the first planet carrier 16a would co-operate directly with the central pin 192 of the trigger 19. Likewise, if there were more than two stages, at least one additional planet carrier would exist between the second planet carrier 16b and the trigger 19.

Figure 16B:
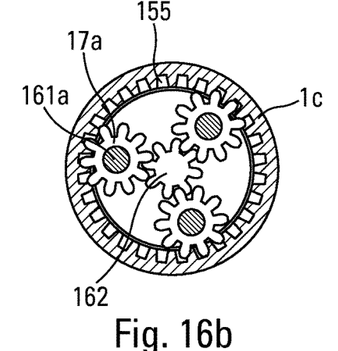
Figure 16C:
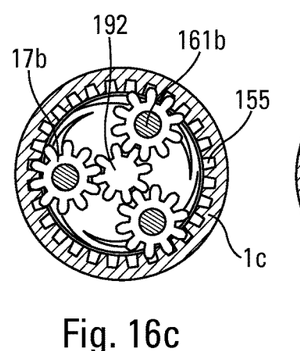
Figure 16D:
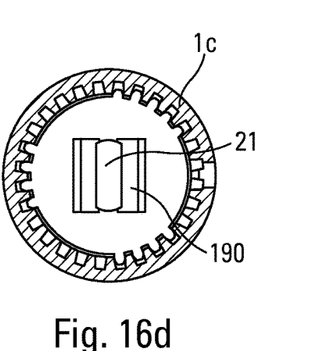

The upper body 1c includes a ring gear 155 on its inside surface, as can be seen clearly in FIGS. 16b and 16c. The ring gear 155 of the upper body 1c co-operates with the planet gears 17a,b that are assembled on the planet carriers 16a,b.

The spiral spring 18 urges the first planet carrier to turn in the direction of arrow F in FIG. 16a. Such turning is transmitted via the planet gears 17a to the central pin 162 of the second planet carrier 16b, and from there, via the planet gears 17b to the central pin 192 of the trigger 19. While the trigger 19 is blocked by said locking key 20, the retarding system is thus also blocked.

When the retarding system is triggered, the spring 18 urges the first planet carrier 16a to turn. The planet gears 17a are thus turned as a result of them meshing with the ring gear 155 of the upper body 1c. Such turning of the planet gears 17a thus causes the central pin 162 of the second planet carrier 16b to turn, and the same operation is repeated with said second planet carrier 16b. The speed of turning of the first planet carrier 16a is thus lower than the speed of turning of said second planet carrier 16b. Each additional stage of the epicyclic gear train forming the retarding system further decreases the rate of turning, and thus further slows down the turning of the first planet carrier 16a. Thus, with two stages as shown in the figures, it is possible to keep the turning of the first planet carrier 16a down to a single turn, while the trigger 19 simultaneously performs about twenty revolutions.

Depending on the number of stages and/or depending on the number of planet gears and/or depending on the shape of the planet carriers and/or depending on the dimensions of the gears used, it is possible to adjust, quite accurately, the time between the moment at which the retarding system is triggered, at the end of injection, and the moment at which the first planet carrier 16a has performed its predefined turning so as to provide the indication, and in particular to indicate in the window of the indicator that the autoinjector may be removed from the injection site. Actuating the visual, audible, and/or tactile indicator device is thus delayed relative to the end of injection, thereby enabling the injected fluid to diffuse in the injection site during this period of delay.

The speed ratio may vary greatly, i.e. the system may be used to slow down the first planet carrier 16a (speed ratio greater than 1), or to slow down the trigger 19 (speed ratio less than 1), e.g. when it is the trigger that forms the indicator element of the visual, audible, and/or tactile indicator device.

As variants to the planet gears co-operating with the ring gear 155 of the upper body 1c, it is also possible to envisage different kinds of transmission, e.g. by friction.

Braking by friction can also be provided, e.g. between the trigger 19 and the ring gear 155 of the upper body 1c. FIG. 17 shows a trigger 19 including three flexible tabs 195a that slide over the ring gear 155 of the upper body 1c so as to brake the turning of said trigger 19.

Figure 18A:
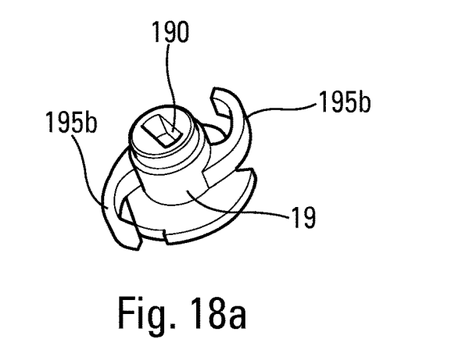
FIGS. 18a and 18b are perspective views of a detail of another variant embodiment.
Figure 18B:
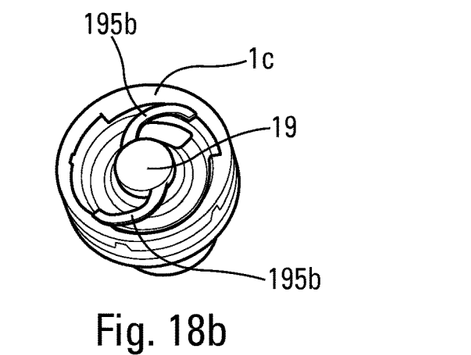

FIGS. 18a and 18b show another variant, in which the trigger 19 includes two flexible tabs 195b, with the ends of the tabs generating a noise throughout the entire time that said trigger 19 is turning, e.g. over an appropriate profile of the upper body, and thereby providing an audible indication that the retarding system is operating: when the noise stops, actuation of the retarding system has ended, and the user may remove the autoinjector from the injection site. Naturally, and simultaneously, the tabs 195b can also brake the turning.

FIG. 19 shows still another variant, in which the trigger 19 includes a flexible tab 195c that may generate noise during turning, and/or brake the turning. In this variant, the trigger includes an inertial mass 196, that promotes braking.

Naturally the variants described above with reference to FIGS. 17 to 19 could also apply to a planet carrier 16a,b rather than to the trigger 19.

The retarding device thus makes it possible to put off the moment at which the indicator indicates the end of use by a predetermined time after the moment at which the injection stage has ended.

A complete actuation stage of the autoinjector is described below.

When the user wishes to use the autoinjector, the user takes hold of the device, e.g. at the body 1, and presses the actuator sleeve 10, which at rest, in its first projecting position, projects out from the lower body 1, against the part of the body where the injection is to be performed. In FIGS. 1a, 1b, and 2a, 2b, it can be seen that the pressure exerted by the user on the actuator sleeve 10 causes said actuator sleeve to slide inside the body 1, thereby uncovering the needle and thus pricking the user as a result of the pressure exerted by the user on the autoinjector.

When the actuator sleeve 10 reaches its actuated position, which is its end position inside the body 1, it causes the injection stage to be triggered, and this is shown in FIGS. 3a, 3b, and 4a, 4b. It should be observed that the piston rod 5 slides inside the syringe A, pushing the piston P of said syringe under the effect of the injection spring 8. The fluid is thus dispensed.

At the end of injection, the retarding system is triggered, in such a manner that the indicator device is actuated only after a predetermined delay.

After indicating the end of use, when the user removes the autoinjector from the injection site, the actuator sleeve 10 once again moves out from the body 1 towards the end-of-use position, which is its second projecting position, under the effect of the spring of the actuator sleeve, with said actuator sleeve 10 being locked, and this guarantees absolute safety for the user and avoids any risk of injury with the needle after the device has been used.

In the embodiment shown, the first and second projecting positions of the actuator sleeve are different positions, however it should be observed that they could optionally be identical.

The present invention applies to devices used in particular for treatment of auto-immune diseases, e.g. of the rheumatoid arthritis, multiple scleroses, Crohn's disease type, for treatment of cancer, for antiviral treatments, e.g. of the hepatitis type, for treatment of diabetes, for treatment of anemia, or for treatment of allergy attacks, e.g. in the event of anaphylactic shock.

Although the present invention is described above with reference to an advantageous embodiment, naturally said embodiment is not limiting. In particular, the actuator sleeve and/or the injection lock and/or the retarding device and/or the audible and/or tactile indicator device could be used and/or made in some other way. Pricking by the needle and/or retracting the needle after injection could be controlled by one or more buttons. Other modifications can also be envisaged by the person skilled in the art, without going beyond the ambit of the present invention, as defined by the accompanying claims.

The invention claimed is:

1. An autoinjector comprising:
a body receiving a reservoir, said reservoir containing fluid and including a piston, said reservoir being stationary in said body;
an actuator sleeve that includes a contact end for coming into contact with an injection site of a user of the autoinjector, said actuator sleeve extending inside said body at least in part, and being movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector;
a piston rod that is adapted to co-operate with the piston of said reservoir, said piston rod being movable between a primed position and an injection position in which said piston rod has moved the piston of the reservoir so as to inject the fluid into the injection site; and
at least one of a visual, audible, or tactile indicator device for indicating to the user that said autoinjector may be removed from said injection site, said visual, audible, and/or tactile indicator device being arranged at a rear end of said body, remote from said injection site;
said autoinjector comprising a retarding device so as to delay actuating said at least one of visual, audible, or tactile indicator device relative to the end of injection, said retarding device comprising an epicyclic gear train having at least one stage said epicyclic gear train comprising a retarding spring, at least one planet carrier, each carrying at least one planet gear, a trigger, and a locking key so as to prevent said trigger from turning until the end of injection, said retarding spring being made in the form of a spiral spring that is fastened firstly to a planet carrier that forms an indicator of said visual, audible, and/or tactile indicator device, and secondly to the body; and
wherein said trigger includes at least one flexible tab that is adapted to co-operate with said body so as to generate a noise or brake the turning of said trigger.

2. The autoinjector according to claim 1, wherein each planet gear of a planet carrier co-operates firstly with said body and secondly either with another planet carrier or with said trigger.

3. The autoinjector according to claim 2, wherein said body includes a ring gear on its inside surface, said ring gear co-operating with at least one planet gear.

4. The autoinjector according to claim 2, wherein said trigger includes a central pin that is provided with a sun gear that co-operates with at least one planet gear.

5. The autoinjector according to claim 1, wherein said epicyclic gear train comprises two planet carriers, each carrying three planet gears.

6. The autoinjector according to claim 1, wherein said locking key comprises a head, a longitudinal rod, and an endpiece that is adapted to co-operate with the piston rod.

7. The autoinjector according to claim 6, wherein, prior to triggering the retarding system, the head of the locking key is in its blocking position in which it co-operates with a corresponding profile of the body and with a corresponding profile of the trigger, such that said trigger is prevented from turning relative to said body by said locking key.

8. The autoinjector according to claim 7, wherein when the piston rod arrives towards its end-of-injection position, it co-operates with the endpiece of the locking key so as to pull said locking key axially downwards out from its blocking position, such that said trigger is thus no longer prevented from turning by said locking key.

9. The autoinjector according to claim 1, wherein said reservoir includes a needle through which said fluid is injected into said injection site.

10. The autoinjector according to claim 1, wherein the reservoir containing fluid and the piston form part of a pre-filled syringe.

11. The autoinjector according to claim 1, wherein the at least one flexible tab is adapted to co-operate with said body so as to generate a noise and brake the turning of said trigger.

12. The autoinjector according to claim 1, wherein said epicyclic gear train has two stages.

* * * * *